(12) United States Patent
Dawson et al.

(10) Patent No.: US 6,770,579 B1
(45) Date of Patent: Aug. 3, 2004

(54) SMART POROUS FILM OR MATERIAL

(75) Inventors: Colin Dawson, Colchester (GB); Julian Vincent, Reading (GB)

(73) Assignee: The Secretary of State for Defense (GB)

( * ) Notice: Subject to any disclaimer, the term of this patent is extended or adjusted under 35 U.S.C. 154(b) by 0 days.

(21) Appl. No.: 10/019,907
(22) PCT Filed: May 10, 1999
(86) PCT No.: PCT/GB99/01470
§ 371 (c)(1),
(2), (4) Date: Mar. 11, 2002
(87) PCT Pub. No.: WO00/68003
PCT Pub. Date: Nov. 16, 2000

(51) Int. Cl.⁷ .............................. B32B 3/10; B32B 3/02; B32B 33/00; D03D 27/00; D04H 11/00
(52) U.S. Cl. ........................ 442/181; 428/131; 428/132; 428/133; 428/134; 428/135; 428/136; 428/137
(58) Field of Search ............................ 428/131–137, 428/88

(56) References Cited

U.S. PATENT DOCUMENTS

| | | | |
|---|---|---|---|
| 3,890,974 A | 6/1975 | Kozak | |
| 5,397,316 A | 3/1995 | LaVon et al. | |
| 5,741,564 A | 4/1998 | Gillberg-LaForce | |
| 5,865,824 A | 2/1999 | Chen et al. | |
| 5,873,868 A | 2/1999 | Nakahata | |

FOREIGN PATENT DOCUMENTS

| | | |
|---|---|---|
| EP | 0122085 | 10/1984 |
| GB | 2254044 | 9/1992 |

*Primary Examiner*—Cheryl A. Juska
*Assistant Examiner*—Lynda Salvatore
(74) *Attorney, Agent, or Firm*—Dean W. Russell; Kilpatrick Stockton LLP

(57) ABSTRACT

A smart film or material which automatically controls its porous properties in relation to changes in its local environment thus allowing fluids to pass through the film or material in a controlled fashion.

15 Claims, 2 Drawing Sheets

SMART POROUS FILM OR MATERIAL

Figure 1:
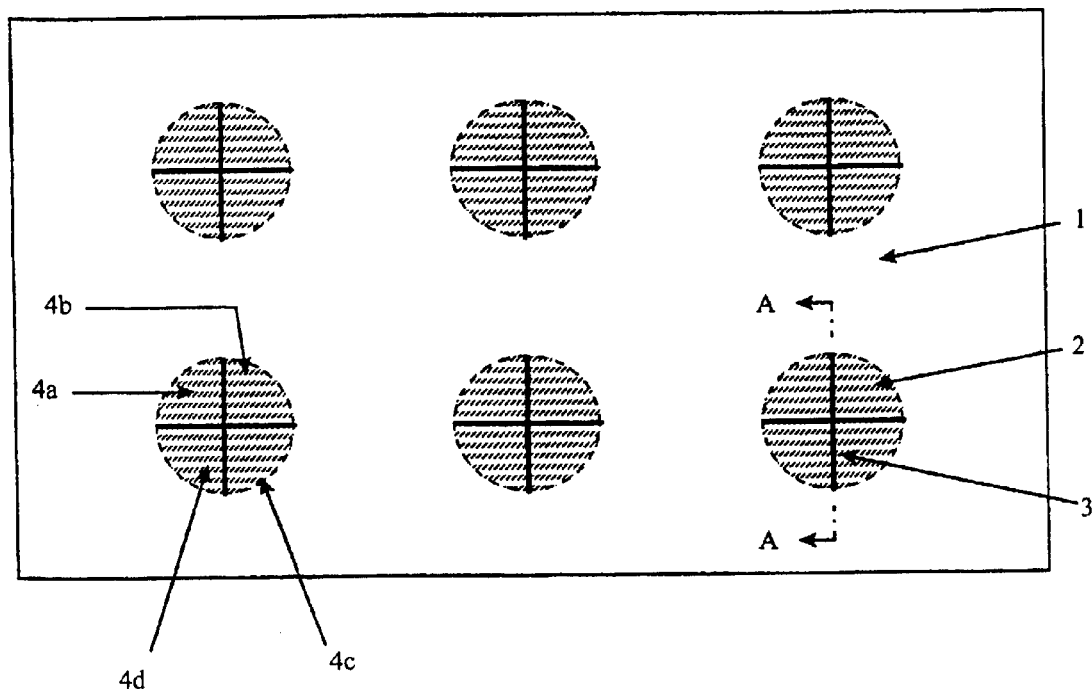

This application claims priority to International Application No. PCT/GB99/01470 filed on May 10, 1999 and published in English as International Publication No. WO 00/68003 on Nov. 16, 2000.

The present invention relates to smart films and materials particularly those which can modify their porous properties and can be used in clothing.

When covering objects with a protective film or material it is often desirable for the film or material to be capable of allowing fluids, such as liquids and gases, to pass from the object through the film or material to the surrounding environment.

Examples of this requirement can be found particularly in clothing where a variety of Moisture Vapour Permeable (MVP) materials are known which allow water vapour to pass through the garment thus removing a proportion of the sweat generated by a wearer. These materials are also widely used in the medical field in the form of bandages and dressings. Also known are materials such as Stomatex (RTM) which is a rubber material having a number of perforations spread throughout the material. The material has pockets below each perforation configured so as to allow a local build up of vapour pressure before allowing the gases through. In both the clothing and medical uses these materials perform their specific function but are limited in that they can only remove gases and vapours and have a limited performance which is constant and does not change in response to environmental changes. Thus under extreme conditions the material will not be able to function satisfactorily. Clothing includes gloves, hats and footwear.

An aim of the present invention is to provide a smart porous film or material which automatically controls its porous properties in relation to changes in its local environment thus allowing fluids to pass through the film or material in a controlled fashion.

Accordingly, the present invention provides a smart film or material comprising at least two layers having different fluid absorption properties wherein all the layers are cut so as to provide a plurality of close fitting flaps through the film or material such that any strain differences between the layers caused by their different fluid absorption properties will cause the flaps to bend providing a plurality of openings in the layer.

As an alternative, the present invention also provides a smart film or material comprising a layer, a surface of which has discrete areas which have fluid absorption properties different to the rest of the layer wherein the discrete areas and the layer which they cover are cut so as to provide a plurality of close fitting flaps through the film or material such that any strain difference between the discrete areas and the layer which they cover, caused by their different fluid absorption properties, will cause the flaps to bend thus providing an opening in the layer.

The bending of the flaps is a result of the layers having different affinities for a fluid in the local atmosphere or the discrete areas having a different affinity for a fluid than layer which they cover.

One example of this effect is where a discrete area has different hydrophilic properties to the layer it covers or the layers have different hydrophilic properties to each other.

In a more specific example a discrete area could be arranged to take in more water or water vapour from the local atmosphere than the layer which it covers it then expands causing a strain difference between it and the layer which it covers. This strain difference causes the flaps to bend in the most energetically favourable direction.

The advantage of the above is that a film or material whose porosity can change in a controlled manner in response to changes in its local environment is provided.

In use the layer or one of the layers can be substantially impermeable such that fluids cannot pass through the film or material except via the openings caused through the film or material. Alternatively the layer or one of the layers can be permeable, in such an embodiment the amount of fluid which can pass through the film or material is increased or decreased by the opening or closing of the flaps through the film or material.

Advantageously one of the layers can be made of a polymer fibre with increased fluid absorption properties such as a polyethylene oxide macromolecular polymer covered by nylon such as Hygra™.

The discrete areas can be produced in the form of materials individually deposited on a surface of the layer, possibly using some form of chemical bond, by a printing process such as dot printing, by transfer coating or spread coating or by any other means which is capable of accurately depositing small amounts of a material on a surface. Alternatively the discrete areas can be produced by an etching process whereby a further layer is attached to the surface of the layer and areas of the further layer are etched away to leave the discrete areas.

The discrete areas deposited on a surface of the layer can be a hydrophilic gel or gel mixture or other suitable material. Such materials may contain, singly or in combination, polyvinyl alcohol, partially hydrolysed polyvinyl acetate, poly(vinylpyrrolidone), polyethylene glycol, ethoxylated polyethylene glycol, polysiloxane, ethoxylated polysiloxane, poly(acrylic acid),copolymers of acrylic acid, poly(N-isopropylacrylamide), poly(2-acrylamide-2-methylpropanesulphonic acid), collagen, gelatin, pectin, starch, in each case optionally cross-linked by incorporation of an appropriate physical cross-linking agent, e.g. borax, or chemical cross-linking agent, e.g. ethylene-bis-acrylamide, and suitable catalysts, e.g. lactic acid, or free radical initiators, e.g. azo-bis-isobutyronitrile, and compatible vegetable or mineral fillers, as has all been described in literature regarding such materials.

The discrete areas can also be formed by locally modifying the layer's fluid absorption properties thus avoiding the need to bond the discrete areas to the layer this can be done by plasma treating a surface of the layer or by treating a surface of the layer with chemicals or radiation. For example, exposing a material composed of an uncrosslinked polymer to a source of high energy radiation (such as UV light or gamma rays) or ionic particles (such as a plasma) it is possible to form crosslinks between the polymer molecules. If the initial starting material is hydrophilic it will be made more hydrophobic by this treatment and the material may also become stiffer.

Advantageously the discrete areas can be only a few millimeters in diameter and can be dispersed over the entire layer, or in specific locations of the layer, in a density defined by the level of porosity required of the film or material. The size of the discrete areas will in practice be limited by manufacturing techniques and the ability to make accurate, small cuts through the film or material.

Obviously larger discrete areas can be provided should large openings be required such as would be needed to allow liquids instead of gases to pass through the film or material.

The cutting of the flaps is preferably done so as to form a plurality of flaps which are located in a close fitting arrangement, i.e. the amount of material removed during cutting should be kept to a minimum. This is advantageous as it aims to maintain as much of the properties of the uncut film or material as is possible. Usefully this can be done using laser, water jet or punching techniques.

Any number of close fitting flaps can be provided at a single location in the film or material however a minimum of 3 flaps will allow the flaps to bend easily providing an opening. Further flaps would increase the size of opening produced at each location, however, the cutting procedure increases in complexity, and the amount of material removed will be increased, as more cuts are needed. The removal of more material will increasingly affect the overall properties of the film or material when the flaps are closed.

An additional improvement of the invention can be obtained by causing a further discrete area which has fluid absorption properties different to the rest of the layer to be formed, which individually surrounds some or all of the discrete areas and is disposed from the discrete area it surrounds. This can be done in the form of a hoop. When the environment adjacent to a further discrete area changes the strain differences between the layer and the further discrete area, as a result of their different fluid absorption properties, causes a pocket or bulge to form in the film or material. Provision of a pocket or bulge beneath the opening formed by the flaps may improve the efficiency of the proposed system. For example, when the pocket or bulge is formed the concentration of a gas, such as water vapour, could be allowed to build up to high levels before the flaps formed in the discrete area are caused, as a result of strain differences between the layers of the flap, to bend thus forming an opening. Once the opening has formed gas exchange between the pocket or bulge and the environment can occur by a process of diffusion. Diffusion is driven by concentration gradients and as such this process of gas exchange is increased by the high concentration of gas in the pocket or bulge and would quickly reduce the level of gas inside the chamber thus allowing the flaps to close. This also reduces the amount of time that the flaps are required to be open.

A film or material according to the present invention can be used in a variety of applications. These applications include use in clothing, medical applications, food wrappings and structures such as tents and garden cloches.

When in use as a clothing material the material can be arranged to have a predetermined porosity which will be capable of being increased by the opening of the flaps in response to changes in the local environment caused by the actions of the wearer. This could possibly be as a result of an increase in the workload of the wearer causing the wearer to become hotter thus requiring an increased amount of fluid, either in the form of moisture vapour or sweat, to be removed from the body. This opening of the flaps could be arranged to occur as a response to an average level of fluid absorption in the film or material or only to occur at extreme levels to reduce heat stress under heavy exertion.

Medical uses of a film or material according to the present invention include uses in bandages or dressings for wounds where it is desirable to either keep the covered area dry or allow gases to escape from the covered area. Again a film or material could be arranged such that the flaps open under average conditions or the flaps could be arranged to open only under extreme conditions.

Uses as food wraps are similar to the medical uses where food needs either to be kept dry or free from a build up of gases. Particular uses in food wraps are where the film or material absorbs gases naturally emitted from the food causing pores to open and thus allowing the gases to be released.

When used in structures such as tents or garden cloches the film or material can prevent the build up of condensation on the inside of the structure or it can allow gases given off from within the structure to escape.

As stated the film or material will be made more porous by the cuts made in it, even when the resulting flaps are closed, unless these cuts can be made to be so close fitting so as to render them impermeable or the cuts are made under tension such that when released the flaps are in close contact with each other. As such the smart film or material may be required to be combined with further materials, possibly using moisture vapour permeable materials or tufted, embedded or woven hairs or fibres, to provide the required overall properties. Another material which could be used is a fur-mimetic material acting as an outer layer to provide protection from rain.

Various materials can be used to produce smart porous textiles according to the present invention. Materials which absorb water and could be coated onto or extruded with a non-absorbing layer include Polyurethanes, Polyether block amides (PEBA), Hydrogels and Water Soluble polymers such as polyvinylpyrrolidone, carboxyl methyl cellulose and polyvinyl alcohol.

The following are, by way of example only, four examples of methods of manufacturing materials in accordance with the present invention:

EXAMPLE 1

A 2×2 200 gsm polyester plainweave fabric is passed through a solution of primer and after drying is stippled with a jet printer dot paste coating and immediately contacted with a powder comprising a 1:1 dry blend of polyvinyl alcohol and polyacrylic acid, pressure being applied by a heated roll at 170 deg C.

The resulting 5 mm diameter adhered disks are present at a surface density of two per square centimeter in a regular grid pattern.

The fabric is subsequently passed intermittently through the work zone of a focused and collimated indexing Carbon Dioxide laser which irradiates each disk area in turn producing cruciform slots each 0.3 mm in width and 3 mm in length through the disk area.

EXAMPLE 2

A previously degreased 300 gsm polyester cored cotton plainweave fabric is passed through the Nitrogen atmosphere work zone of an indexed scanning electron beam (300 KeV, 15 mA) traversing the full width of fabric at a lateral sweep velocity of 25 m/min.

Acrylic Acid is sprayed onto one side of the fabric in striated zones and the fabric passed through a drying oven at 100 deg C. with a residence time of 10 minutes followed by cooling to room temperature over a further 10 minutes with fan assist.

The add on weight of polyacrylic acid is 200 gsm in the areas treated.

The fabric is subsequently punched with a cruciform pattern in the region of the striations only to give a pore density of one pore per square centimeter, the pores being 5 mm long in each orthogonal direction.

EXAMPLE 3

A previously degreased 300 gsm polyester cored cotton plainweave fabric is activated by electron beam exposure in selected zones and is then fully coated with N-vinylpyrrolidone containing 0.5% by weight of N.N-mythylene-bis-acrylamide. The fabric could also be activated chemically by treatment with any of peroxydisulphuric acid, chromic acid, ferric chloride/hydrogen peroxide or peroxyacetic acid.

The fabric is passed through a ventilated drying oven at 70 degrees C. with residence time of 10 minutes followed by a further 10 minutes cooling with fan assist.

The fabric is then passed through a water bath with agitation to dissolves away the unfixed coating leaving a fabric having poly(N-vinylpyrrolidone) coating (200 gsm) in irradiated zones only.

The fabric is then punched to form cruciform cuts.

EXAMPLE 4

An A4 specimen of 60 gsm microfibre polyester woven fabric is laid on foil and the exposed surface treated for 10 minutes in a cold plasma barrel reactor with a maintained rarefied atmosphere of nitrogen containing 20% v/v N-vinylpyrrolidone (0.05 Torr) excited by a 100W microwave field (433 MHz).

The polyester fabric is then exposed to a scanning and indexing $CO_2$ laser to receive cruciform cuts.

The textile has become hydrophilic on one side, while remaining hydrophobic on the other.

An embodiment of the present invention will now be described, by way of example, with reference to the accompanying drawings, wherein FIG. 1. Shows a plan view of a smart porous material according to the present invention, the stippled areas indicating the smart discrete areas of the material.

Figure 2:
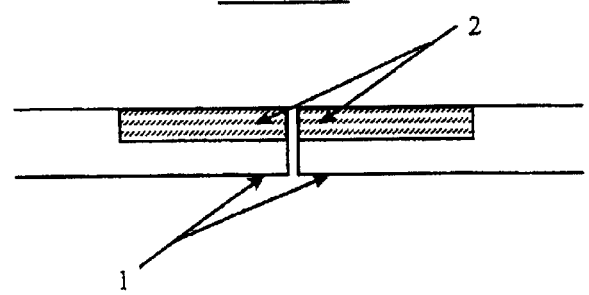

FIG. 2. Shows a section A—A through the material shown in FIG. 1.

Figure 3:
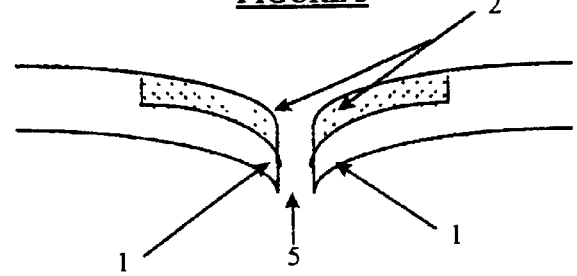

FIG. 3. Shows the same cross section as in FIG. 2 following opening of the flaps.

Figure 4:
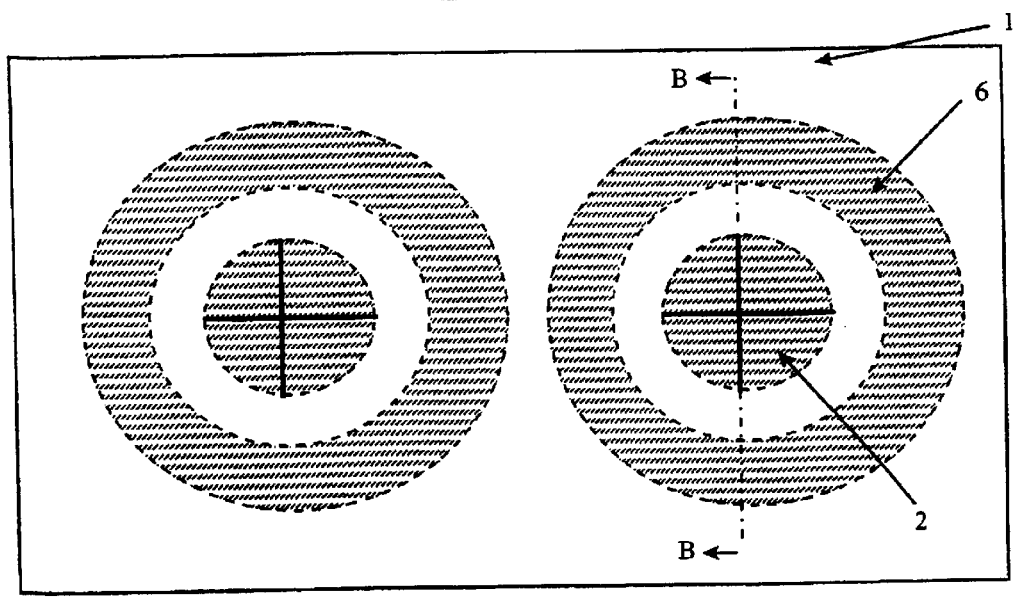

FIG. 4. Shows a plan view of an improved smart porous material according to the present invention, the stippled areas indicating the smart discrete areas of the material.

Figure 5:
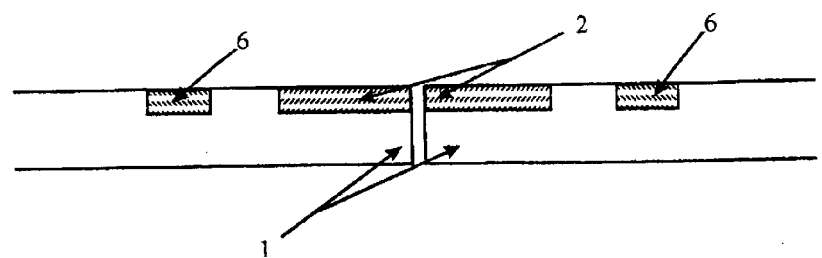

FIG. 5. Shows a section B—B through the material shown in FIG. 4.

Figure 6:
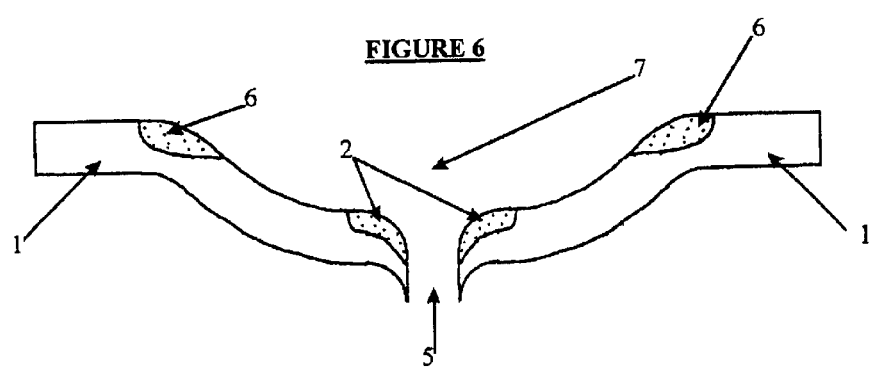

FIG. 6. Shows the same cross section as in FIG. 5 following formation of the pocket and opening of the flaps.

A smart porous material according to the present invention is shown in FIG. 1 and comprises a layer (1), on which is arranged humidity sensitive discrete areas (2) which have different hydrophilic properties to the layer. These areas can be produced by plasma treatment of specific areas of the layer. Thus changing the hydrophilic properties of a relatively thin area (2) at the surface of the layer (1). The humidity sensitive discrete areas are arranged and sized so as to fit as many discrete areas on the layer as is required to give the necessary porous properties. Each discrete area and the layer beneath it is then cut, using laser techniques in the form of a cross (3), thus providing 4 flaps (4 a, b, c & d), two of which are shown in cross section in FIG. 2. When the humidity of the environment adjacent to a humidity sensitive discrete area increases the flaps will be caused to bend due to the strain differences caused by the different hydrophilic properties of the layer and discrete area, as shown in FIG. 3, thus causing an opening (5) to be formed in the material and causing the material as a whole to become more porous. When the humidity of the environment adjacent to the same discrete area decreases it will cause the flaps to straighten thus closing the opening and causing the material as a whole to become less porous, as shown in FIG. 2.

An improvement of the invention can be obtained by causing a further humidity sensitive discrete area (6), as shown in FIGS. 4 and 5, to be formed in a hoop outside some or all of the discrete areas (2). As shown in FIG. 6, when the humidity of the environment adjacent to a further discrete area increases the strain differences between the layer (1) and further discrete area (6), as a result of their different hydrophilic properties, causes a pocket (7) as well as the hole (5) to form in the material thus increasing the overall material's ability to transfer moisture. The hole (5) and the pocket (7) can be arranged to form at a similar humidity level or at different humidity levels.

What is claimed is:

1. A smart film or material comprising a layer, a surface of which has discrete areas which have fluid absorption properties different to the rest of the layer wherein the discrete areas and the layer which they cover are cut so as to provide a plurality of close fitting flaps through the film or material such that any strain difference between the discrete areas and the layer which they cover, caused by their different fluid absorption properties, will cause the flaps to bend thus providing an opening in the layer.

2. A smart film or material according to claim 1 configured so as to be suitable for use in clothing.

3. A smart film or material according to claim 1 wherein the discrete areas are produced by attaching a material having different fluid absorption properties to the surface of the layer.

4. A smart film or material according to claim 1 wherein the discrete areas are areas of the layer which have been plasma treated or treated with chemicals or radiation so as to modify their fluid absorption properties.

5. A smart film or material according to claim 1 wherein the discrete areas are provided by a printing process.

6. A smart film or material according to claim 1 wherein the discrete areas are provided by an etching process.

7. A smart film or material according to claim 1 wherein the discrete areas and the layer which they cover or all the layers are cut using a laser or a punch.

8. A smart film or material according to claim 1 wherein at least some of the discrete areas are individually surrounded by a further discrete area which has fluid absorption properties different to the rest of the layer, the further discrete area being disposed from the discrete area which it surrounds.

9. A smart film or material according to claim 8 wherein at least one of the further discrete areas is provided in the form of a hoop.

10. A smart film or material according to claim 1 wherein the layer or one of the layers is permeable.

11. A smart film or material according to claim 1 which forms one element of a multi-element textile.

12. A smart film or material according to claim 1 wherein the layers have different hydrophilic properties to each other.

13. A smart film or material according to claim 1 wherein the layer and the discrete areas have different hydrophilic properties.

14. A smart film or material according to claim 1 wherein the discrete areas and the layer which they cover or all the layers are cut so as to provide at least 3 close fitting flaps through the film or material.

15. A smart film or material according to claim 1 wherein the layer or one of the layers is substantially impermeable.

* * * * *

UNITED STATES PATENT AND TRADEMARK OFFICE
CERTIFICATE OF CORRECTION

PATENT NO.    : 6,770,579 B1                                              Page 1 of 1
DATED         : August 3, 2004
INVENTOR(S)   : Colin Dawson and Julian Vincent It is certified that error appears in the above-identified patent and that said Letters Patent is hereby corrected as shown below:

<u>Title page,</u>
Item [73], Assignee's name should be -- The Secretary of State for Defence (GB) --

Signed and Sealed this

Twenty-first Day of December, 2004

JON W. DUDAS
*Director of the United States Patent and Trademark Office*